(12) United States Patent
Chen

(10) Patent No.: US 8,501,164 B2
(45) Date of Patent: Aug. 6, 2013

(54) NICOTINE LOZENGE COMPOSITIONS

(75) Inventor: Li-Lan Chen, Parsippany, NJ (US)

(73) Assignee: GlaxoSmithKline, LLC, Philadelphia, PA (US)

( * ) Notice: Subject to any disclaimer, the term of this patent is extended or adjusted under 35 U.S.C. 154(b) by 45 days.

(21) Appl. No.: 12/990,049

(22) PCT Filed: Apr. 30, 2009

(86) PCT No.: PCT/US2009/042190
§ 371 (c)(1),
(2), (4) Date: Oct. 28, 2010

(87) PCT Pub. No.: WO2009/134947
PCT Pub. Date: Nov. 5, 2009

(65) Prior Publication Data
US 2011/0110880 A1    May 12, 2011

Related U.S. Application Data

(60) Provisional application No. 61/049,515, filed on May 1, 2008.

(51) Int. Cl.
*A61K 31/787* (2006.01)
*A61P 25/34* (2006.01)

(52) U.S. Cl.
USPC ..................................... 424/78.15

(58) Field of Classification Search
None
See application file for complete search history.

(56) References Cited

U.S. PATENT DOCUMENTS

| | | | |
|---|---|---|---|
| 4,863,737 A | 9/1989 | Stanley et al. | |
| 4,967,773 A | 11/1990 | Shaw | |
| 5,135,753 A | 8/1992 | Baker et al. | |
| 5,549,906 A | 8/1996 | Santus | |
| 6,183,775 B1 | 2/2001 | Ventouras | |
| 7,767,698 B2 | 8/2010 | Warchol et al. | |
| 8,075,911 B2 | 12/2011 | Gale | |
| 2003/0133982 A1 | 7/2003 | Heimlich et al. | |
| 2004/0052851 A1 | 3/2004 | Graff et al. | |
| 2004/0191322 A1 | 9/2004 | Hansson | |
| 2005/0053665 A1 | 3/2005 | Ek et al. | |
| 2005/0123502 A1* | 6/2005 | Chan et al. | 424/78.3 |
| 2007/0081949 A1 | 4/2007 | Dam et al. | |
| 2007/0269492 A1 | 11/2007 | Steen et al. | |
| 2007/0298090 A1 | 12/2007 | Chen et al. | |
| 2008/0286341 A1 | 11/2008 | Andersson et al. | |
| 2008/0302375 A1 | 12/2008 | Andersson et al. | |

FOREIGN PATENT DOCUMENTS

| | | |
|---|---|---|
| EP | 707478 B1 | 2/1995 |
| EP | 1404306 B1 | 12/2002 |
| EP | 2152313 A1 | 11/2008 |
| EP | 2233134 A1 | 3/2010 |
| FR | 2792200 | 10/2000 |
| WO | WO2006124366 | 11/2006 |
| WO | WO2007/104575 | 9/2007 |
| WO | WO2007133140 A1 | 11/2007 |
| WO | WO2007133141 A1 | 11/2007 |
| WO | WO2008140371 A1 | 11/2008 |
| WO | WO2008140372 A1 | 11/2008 |
| WO | WO2008140373 A1 | 11/2008 |
| WO | WO2009006095 A2 | 1/2009 |
| WO | WO2010044736 A1 | 4/2010 |
| WO | WO2011038101 | 3/2011 |

* cited by examiner

*Primary Examiner* — Suzanne Ziska
*Assistant Examiner* — Thurman Wheeler
(74) *Attorney, Agent, or Firm* — Joshua C. Sanders; Theodore R. Furman

(57) ABSTRACT

The present invention relates to nicotine lozenge compositions comprising reduced levels of buffering agents from traditional nicotine lozenges and which provide optimal oral pH and prompt nicotine absorption in a smaller, more convenient dosage form.

22 Claims, 3 Drawing Sheets

NICOTINE LOZENGE COMPOSITIONS

This application is a 371 of International Application No. PCT/US2009/042190, filed 30 Apr. 2009, which claims the benefit of U.S. Provisional Application No. 61/049,515, filed 1 May 2008, which is incorporated by reference herein in its entirety.

FIELD OF THE INVENTION

The present invention relates to nicotine lozenge compositions which have improved sensory profiles and user compliance. The present invention further relates to nicotine lozenge compositions which comprise reduced levels of buffering agents that provide an optimal oral pH and, thus, enhance nicotine absorption through oral or mucosal tissues.

BACKGROUND OF THE INVENTION

It is generally known that active as well as passive smoking of tobacco products, such as cigarettes, cigars and pipe tobacco presents serious health risks to the user and those subjected to secondary smoke. It is also known that the use of smokeless forms of tobacco, such as chewing tobacco, spit tobacco and snuff tobacco, presents serious health risks to the user. Furthermore, the use of tobacco products in public areas is increasingly either restricted or socially unacceptable. Consequently, smokers and other tobacco users often try to quit the potentially deadly habit. Others may be forced to cut back on the amount of tobacco used as employment and social settings increasingly restrict smoking and other tobacco use.

Although the damaging effects of tobacco usage are well known, most individuals who are nicotine dependent have great difficulty in overcoming their dependence on nicotine, typically in cigarette form. The difficulty arises in part due to the highly addictive nature of nicotine and the strong nicotine withdrawal symptoms that can occur when one begins to deprive the body of the nicotine to which it has grown dependent. Indeed, overcoming nicotine withdrawal symptoms is a critical challenge for those attempting to conquer nicotine dependence.

Nicotine withdrawal symptoms, particularly nicotine cravings, may arise in several ways. For instance, studies have shown that following a quit attempt, smokers report moderate levels of steady nicotine craving throughout the day. This craving can prove too much for some, leading to relapse and a return to tobacco usage for some of those individuals attempting to quit. In addition to steady cravings, smokers may also experience episodic, or acute, cravings. These acute cravings may be provoked by a number of stimuli, such as exposure to smoking related cues, seeing smoking paraphernalia, being in proximity to others engaged in smoking, or inhaling second hand smoke. Such episodic cravings may also lead to relapse if effective coping measures are not employed by the individual.

In an attempt to assist those who wish to eliminate or reduce tobacco usage, efforts have been made to provide those in need with some level of nicotine craving relief. Historically, these efforts have focused on the activity and administration of nicotine itself. This nicotine replacement therapy (NRT) helps to combat the intense nicotine withdrawal symptoms encountered by many individuals upon quitting smoking or other tobacco usage. In recent years, NRT has been successfully commercialized in both the United States and elsewhere. Such commercial NRT offerings include nicotine gums, and nicotine transdermal patches (e.g., NICODERM® brand patches and NICORETTE® brand gums sold by GlaxoSmithKline Consumer Healthcare).

In addition to traditional gums and patch NRT offerings, more recently, nicotine containing lozenges have been introduced commercially both within and outside the United States. For example, COMMIT®, brand lozenges offer individuals an alternative form of NRT. U.S. Pat. No. 5,110,605 to Acharya et al. relates to lozenge compositions which comprise polycarbophil and alginic acid components. Other examples of nicotine containing lozenge formulations are found in a number of publications, including but not limited to, U.S. Pat. No. 4,967,773 to Shaw; U.S. Pat. No. 5,549,906 to Santus; U.S. Pat. No. 6,183,775 to Ventouras; and WO 2007/104575 to Axelsson et al. Similarly, U.S. Pat. Nos. 5,593,684; 5,721,257 and 5,362,496 (all to Baker et al.) disclose methods and therapeutic systems for smoking cessation, utilizing both transdermal nicotine delivery for obtaining base-line nicotine plasma levels, and transmucosal administration of nicotine to satisfy transient cravings. While such means are useful as aids to reduce or quit smoking, there is an ongoing need to provide improved lozenge formulations to assist individuals in quitting nicotine usage. In particular, there remains a need to develop lozenge forms which provide the traditional levels of craving relief to an individual but are designed to improve user compliance with an NRT program. In particular, a smaller lozenge, with comparable or faster dissolution time and onset of craving relief would boost user compliance with an NRT regimen and would be advantageous.

The present invention provides nicotine lozenge formulations with improved organoleptics, improved onset of delivery and reduced dissolution time in the oral cavity and, thereby, improved user compliance.

SUMMARY OF THE INVENTION

The present invention relates to nicotine containing lozenge compositions which comprise lower levels of alkaline buffering agents than traditional nicotine containing oral dosage forms while achieving optimal and palatable oral pH and enhancing nicotine absorption through the oral cavity. The present invention comprises alkaline buffering agents both within and external to a master granulation, while overall incorporating lower levels of the alkaline buffering agent within the composition versus traditional lozenges in which the buffering agents are uniformly dispersed in the intragranular portion. Advantageously, the compositions of the present invention can be formulated in much smaller lozenge than traditional nicotine containing lozenges and, thus, have reduced dissolution times in the oral cavity while still achieving significant nicotine plasma level and obtaining comparable nicotine pharmacokinetic profiles to the traditional lozenge. By reducing dissolution time, optimizing the oral pH and improving the speed of nicotine absorption, patient compliance is also improved.

DETAILED DESCRIPTION OF THE INVENTION

Figure 1:
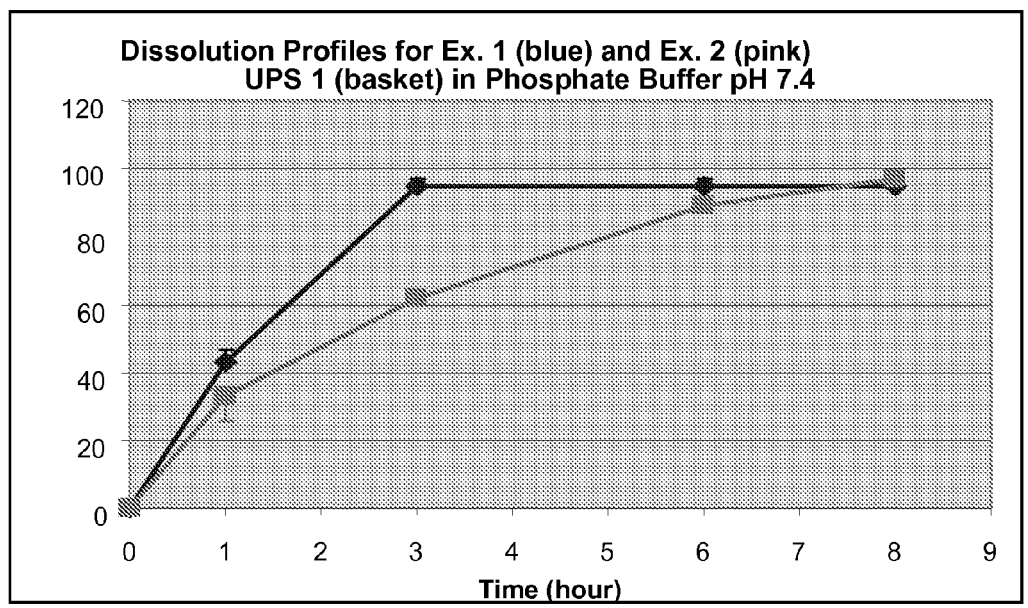
FIG. 1 depicts the dissolution profile (as % release versus time) of a nicotine containing lozenge of the formulation of Example 1 wherein the buffering agent is present both within and extragranular to the master granules versus a lozenge of the formulation of Example 2 wherein all buffering agent is present intragranular to the master granules. USP apparatus I was used to conduct the dissolution study.

All publications including, but not limited to, patents and patent applications cited in this specification are incorporated herein by reference as though fully set forth.

Unless otherwise specified all parts and percentages set forth herein are weight percentages based on the total weight of the relevant orally dissolving lozenge being described.

Unless otherwise stated as used herein, the term "a" or "an" includes one or more of the components modified.

The present invention may comprise, consist of, or consist essentially of the components set forth below, unless otherwise stated.

As described above, the formulations of the present invention comprise a master granule component as well as an extragranular component.

The use of "master granule" formulations is common in solid dosage forms such as tablets and compressed lozenges. Typically, the master granulation is made to improve the processability of a solid dosage form and to reducing friability during transportation and handling. In the absence of a master granule component, tablets or lozenges where high levels of non-direct compressible diluents are used can be difficult to process or result in a product with high friability. In a typical nicotine lozenge formulation, such as that of the COMMIT lozenge, fillers or diluents (hereinafter collectively referred to as "diluents") and dissolution modifiers or binding agents (hereinafter collectively referred to as "dissolution modifiers") are generally granulated together along with buffering agents to form these master granules. Active agents, and other optional excipients and flavoring agents, are thereafter blended with the master granules, prior to compressing, and make up the "extragranular" component of these traditional lozenge formulations.

In contrast, however, in the formulations of the present invention, the master granules comprise at least one diluent, at least one dissolution modifier and at least one buffering agent. The master granules are then combined with a nicotine active, additional alkaline buffering agent and, optionally, taste masking agents, flavors, sweeteners, chelating agents, anti-oxidants or preservatives, processing aids such as glidants or lubricants, or colorants.

As used herein, the term "nicotine active" refers to one or more compounds selected from: nicotine; derivatives of nicotine, such as nicotine salts and nicotine complexes; tobacco extract or leaf; any compounds or compositions that produce a similar physiological effect as nicotine, such as lobeline; and mixtures thereof. A variety of nicotine actives are well known in the art and are commercially available. Suitable nicotine actives for use herein include, but are not limited to, nicotine monotartrate, nicotine bitartrate, nicotine hydrochloride, nicotine dihydrochloride, nicotine sulfate, nicotine zinc chloride monohydrate, nicotine salicylate, nicotine oil, nicotine complexed with cyclodextrin, polymer resins such as nicotine polacrilex, and mixtures thereof. The nicotine active may be used in one or more distinct physical forms well known in the art, including free base forms, encapsulated forms, ionized forms and spray-dried forms. In one embodiment, the nicotine active is the nicotine polacrilex.

In one embodiment the nicotine polacrilex is present in an amount from about 1 mg to about 10 mg of nicotine base per dosage form. The percentage of nicotine polacrilex per dosage form is from about 2% to about 20% of the total weight of the dosage form.

Importantly, in the present invention, both the nicotine active and the counter ions from the alkaline buffering agent exist in the extra-granular space within the present formulations. Where the nicotine active is a polymer resin, such as nicotine polacrilex, nicotine forms an ionic complex with polacrilex which is stable and water insoluble. Once administered, the release of nicotine from the polymer resin complex occurs through an ionic exchange process with counter ions that also become available through dissolution in the oral cavity. This results in the release of free nicotine from the water insoluble resins which is then ready for absorption through the oral mucosa. In a traditional lozenge formulation, more than double the amount of buffering agents of the present invention are incorporated within the master granule only. Upon disintegration, nicotine is still bound to the polacrilex as there are not sufficient cations in the saliva to exchange and release the nicotine from the complex. Thus, the nicotine of these traditional lozenges is not available until the master granules dissolve and release the buffer (counter ions) in the oral cavity. Because the buffering agents are granulated with the binding dissolution modifiers the release of the buffering agents is somewhat slowed. Once released, the buffer first exchanges with the nicotine, and then must raise the pH of the oral cavity to prompt nicotine absorption through the mucosal tissues. As a result, there is delay before the absorption of nicotine from these traditional lozenges occurs.

By incorporation of the buffering agents, both within and external to the master granules, it has been found that lower levels of the buffering agents are needed to achieve optimal and palatable pH in the oral cavity and faster nicotine absorption. In the current invention, the nicotine is immediately freed from the nicotine polacrilex complex by the presence of the counter ions available in the extragranular buffering agent upon disintegration. Thus, all buffering agent later released from the master granules is available to raise the oral cavity pH and drive nicotine absorption through the mucosal tissues. It is, thus, important that no dissolution modifiers are present in the extragranular portion of the formulation as this may retard the increase in oral pH by slowing the dissolution of the extragranular portion of the formulation.

Figure 2:
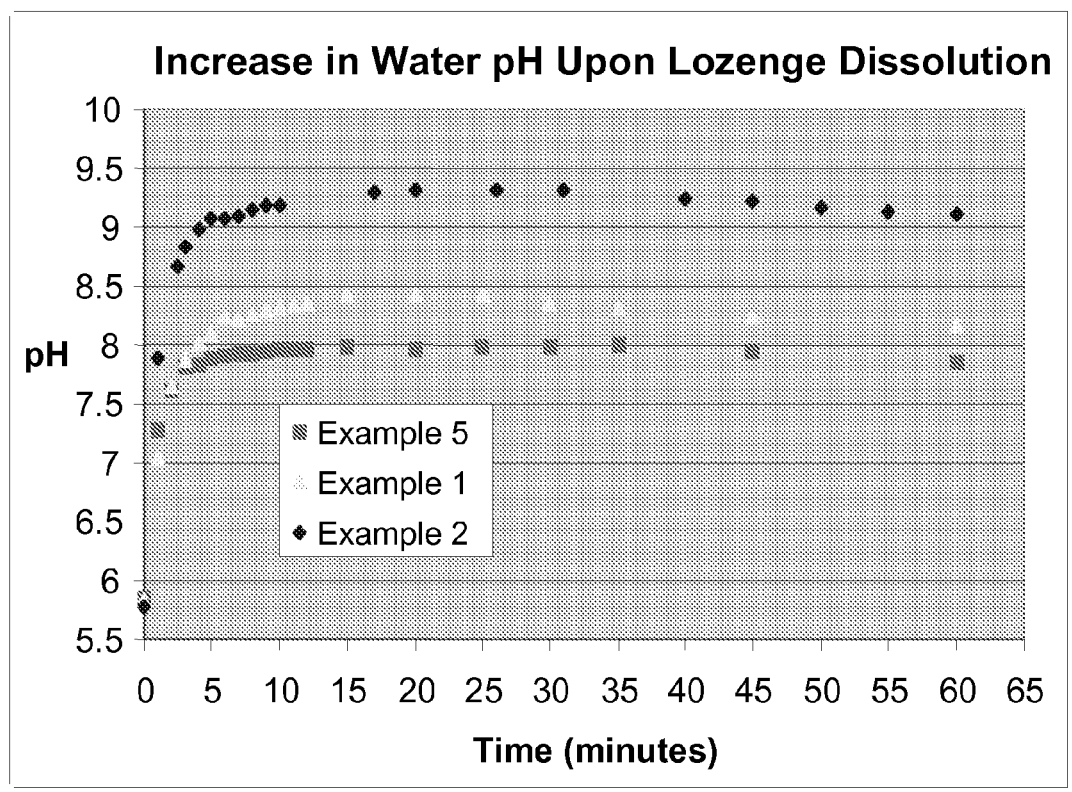
FIG. 2 depicts the pH in water over time upon dissolution of a lozenge of the formulation of Example 1 versus that of a lozenge of the formulation of Example 2 and that of Example 5 wherein all buffering agent is present intragranular to the master granules. USP disintegration apparatus was used to measure the water pH increased upon disintegration and dissolution of lozenges.

FIG. 2 depicts the increase in pH achieved by the formulations of the present invention (Example 1) versus lozenges wherein the buffering agents are completely subsumed within the master granulation (Examples 2 and 5). In particular, where similar low levels of buffers are used (Example 1 vs. Example 6), the maximum pH achieved is indeed higher, where the buffering agent is present both within and external to the master granule, rather than within the master granule only. In addition, FIG. 2 depicts that a substantial reduction in buffering agents is still sufficient to achieve optimal pH to drive nicotine absorption when the buffer is present both within and external to the master granules. (Example 2 vs. Example 1).

Alkaline buffering agents suitable for use in the present invention include, but are not limited to, sodium carbonate, sodium bicarbonate, potassium phosphate, potassium carbonate and potassium bicarbonate. In one embodiment, the buffering agents are selected from potassium bicarbonate, sodium carbonate and mixtures thereof. The buffering agents are incorporated within the master granules as well as incorporated within the extra-granular space between said master granules. The total amount of buffer present in the compositions of the present invention is from about 5 mg to about 20 mg. In one embodiment the total amount of buffer present in the compositions of the present invention is from about 8 mg to about 12 mg. In one embodiment the ratio of nicotine polacrilex to total buffer is from about 3:1 to about 1:3 by total weight.

As indicated above the alkaline buffering agents are incorporated both within the master granules (intragranular) and within the extragranular space between said master granules (extragranular). In general, the amount of buffering agent present in the compositions of the present invention, expressed as a ratio of intragranular buffering agent to extragranular buffering agent is from about 5:1 to about 1:5. In one embodiment, the ratio of intragranular buffering agent to extragranular buffering agent is about 1:1.

Master granules for use in the present formulations are prepared through wet or dry granulation processes which would be apparent to one of skill in the art.

In one embodiment, a wet granulation technique is employed, wherein the at least one dissolution modifier, and the at least one buffering agent is preblended. The preblended mixture and at least one filler is combined and wetted with purified water. This combination is then fed to an extruder where it is compressed and granules are formed. The resultant granules are dried, using any method known in the art, such as fluid bed drying. The master granules are then screened for suitable particle size, typically 75 um, 200 mesh. The master granules are then blended with the nicotine active, at least one buffering agent, flavorants and sweeteners. Upon mixing and screening of this mixture, a lubricant or glidant is added to the mixture. This final blend is then compressed into a suitable lozenge.

The unit weight of lozenges of the present invention is from about 100 mg to about 500 mg total weight per lozenge. In one embodiment the unit weight of the present lozenges is about one quarter that of a conventional lozenges, such as a COMMIT® lozenge (total unit weight of 1.2 gms). In one embodiment the present lozenges are 200 mg to 300 mg total weight per lozenge.

Fillers suitable for use within the master granules of the present invention include, but are not limited to, maltitol, maltose, fructose, glucose, trehalose, sorbital, sucrose, sugar, mannitol, xylitol, isomalt, dextrose, maltodextrin, dextrates, dextrin, erythritol, lactitol, polydextrose and mixtures thereof. In one embodiment, the filler is mannitol. In one embodiment, the mannitol is present from about 100 mg to about 300 mg per lozenge, in another embodiment from about 150 mg to about 200 mg per lozenge.

Dissolution modifiers suitable for use in the present invention include, but are not limited to, acacia, agar, alginic acid or a salt thereof, carbomer, carboxymethylcellulose, carrageenan, cellulose, chitosan, copovidone, cyclodextrins, ethylcellulose, gelatin, guar gum, hydroxyethyl cellulose, hydroxyethyl methylcellulose, hydroxypropyl cellulose, hypromellose, inulin, methylcellulose, pectin, polycarbophil or a salt thereof, polyethylene glycol, polyethylene oxide, polyvinyl alcohol, pullulan, starch, tragacanth, trehalose, xanthan gum and mixtures thereof. In one embodiment, the dissolution modifiers included within the formulations of the present invention are selected from the group consisting of alginic acid or a salt thereof, polycarbophil or a salt thereof, xanthan gum and mixtures thereof. In one embodiment, sodium alginate, calcium polycarbophil and xanthan gum are incorporated within the master granules of the present invention. The amount of dissolution modifier present in the master granules of the present invention is from about 10 mg to about 30 mg per lozenge, in another embodiment from about 15 mg to about 25 mg per lozenge.

Optional excipients may also be incorporated in the formulations of the present invention. These optional excipients may include taste masking agents.

Taste masking agents suitable for incorporation within the extra-granular space of the present invention include intensive sweetening agents and/or flavorants. Suitable intensive sweetening agents include, but are not limited to, aspartame, acesulfame K, cyclamate and salts thereof, glycyrrhizin and salts thereof, neohesperidine, sucralose, saccharin and salts thereof, thaumatin and mixtures thereof. Suitable flavorants include, but are not limited to, menthol, peppermint, wintergreen, sweet mint, spearmint, vanillin, chocolate, coffee, cinnamon, clove, tobacco, citrus and fruit flavors and mixtures thereof. When present, taste masking agents are present in an amount from about 1 mg to about 50 mg per lozenge.

Additional optional excipients may also be included in the formulations of the present invention, such as processing and stabilizing aids. Processing and stabilizing aids include, but are not limited to, chelating agents, anti-oxidants or preservatives, glidants or lubricants, or colorants. Antioxidants/preservatives suitable for use in the present invention may include sodium benzoate, butyl-hydroxy toluene and tocopherol and its salts. Glidants/lubricants suitable for use herein include, but are not limited to, talc, corn starch, stearic acid, calcium stearate, polyethylene glycol, colloidal silicon dioxide, sodium stearyl fumarate, magnesium stearate, vegetable and mineral oils and mixtures thereof. In one embodiment the lubricant is magnesium stearate. Suitable colorants for use herein include any pigments, dyes, lakes or natural food colors that are suitable for food and drug applications, eg. FD&C dyes and lakes. Where processing and stabilizing aids are incorporated within the extra-granular portion of the present invention, the total of such aids is from about 1 mg to about 25 mg per lozenge.

Lozenges of the present invention are useful as a tobacco replacement, and as a means to reduce or stop tobacco use. The compositions may be used as a total or partial replacement of tobacco, and may be used concurrently with tobacco as part of a planned tobacco reduction program, e.g., while reducing tobacco usage prior to outright quitting tobacco usage. A user may consume a lozenge of the present invention at set intervals throughout the day as part of a tobacco quit regime. Alternatively, a user may consumer a lozenge of the present invention intermittently in response to an acute nicotine craving. In one embodiment a user may consumer a lozenge of the present invention at both predetermined intervals as well as intermittently throughout the day to assist with craving relief.

Lozenges of the present invention are intended to deliver the same amount of nicotine to an individual as traditional NRT lozenge or gum products. However, lozenges of the present invention are smaller than traditional lozenges, and dissolve more rapidly once administered to the oral cavity of the user. In one embodiment the in vivo dissolution time of a lozenge of the present invention ranges from about 5 minutes to about 25 minutes and on average the in vivo dissolution time is about 10 times faster than that of a traditional lozenge. In another embodiment, the in vivo dissolution time of a lozenge of the present invention is less than about 15 minutes. This shortened retention time in the mouth results in improved user compliance, i.e. a user is more likely to suck a lozenge to completion and therefore experience the maximum benefit.

Figure 3:
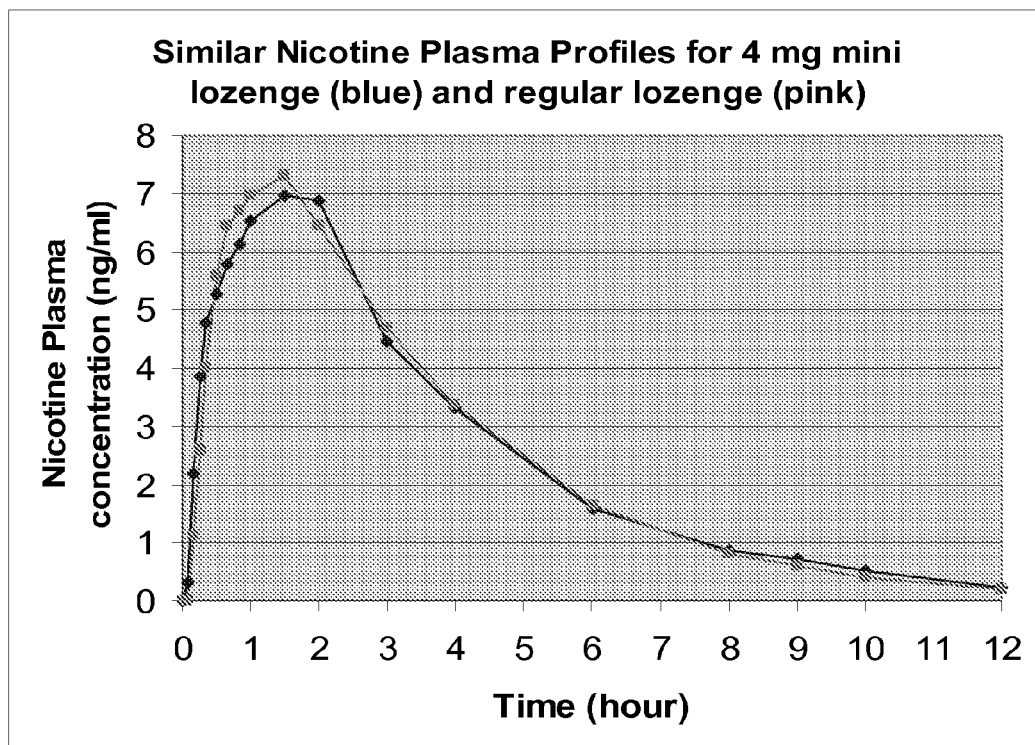
FIG. 3 depicts the nicotine plasma concentration of a lozenge of the present invention (Example 1) versus that of a traditional lozenge (Example 2) in healthy smokers.

FIG. 3 demonstrates the bioequivalence of a formulation of the present invention versus the formulation of a traditional lozenge. The extent (Cmax) and total exposure (AUC) of nicotine delivered by the current invention is the same as that delivered by a traditional lozenge.

The present invention also relates to methods of reducing tobacco usage, comprising administering a composition of the present invention to a person in need thereof. The present invention also relates to a method of reducing nicotine withdrawal symptoms comprising administering the compositions of the present invention to a person in need of such relief. "Need" is intended to include a person's desire to reduce tobacco usage or nicotine withdrawal symptoms, respectively. "Reducing" nicotine withdrawal symptoms or tobacco usage includes eliminating nicotine withdrawal symptoms or tobacco usage.

EXAMPLES

Without further elaboration, it is believed that one skilled in the art can, using the preceding description, utilize the present invention to its fullest extent. The following examples, therefore, are to be construed as merely illustrative and not a limitation of the scope of the present invention.

Examples 1, 3 and 4 exemplify the formulations of the current invention. Examples 2 and 5 are supplied for comparative purposes. Example 2 is a traditional lozenge composition wherein all buffering agents are present in the master granules. Example 5 is a lozenge composition wherein all buffering agents are present in the master granules, but wherein the total amounts of potassium bicarbonate and sodium carbonate are comparable to those present in Examples 1, 3 and 4 of the present invention.

Examples 1-5 are prepared in the following manner: (1) master granules are first prepared by wet granulation of the ingredients listed and are then subsequently dried, (2) the master granules are then mixed with the remaining ingredients, and (3) the combined mixture is compressed into 250 mg total weight lozenges

TABLE 1

Formulations of the Present Invention and Comparative Examples

|  | Example 1 | Example 2 | Example 3 | Example 4 | Example 5 |
|---|---|---|---|---|---|
| Master granules | 187.33 | 1158.57 | 198.44 | 201.22 | 424.22 |
| Mannitol | 165.79 | 1025.34 | 175.62 | 178.08 | 375.43 |
| Potassium bicarbonate | 0.45 | 2.80 | 0.48 | 0.48 | 1.02 |
| Sodium carbonate | 3.67 | 22.75 | 3.89 | 3.94 | 8.31 |
| Sodium alginate | 10.30 | 63.70 | 10.91 | 11.07 | 23.33 |
| Calcium polycarbophil | 5.13 | 31.73 | 5.44 | 5.51 | 11.62 |
| Xanthan gum | 1.99 | 12.25 | 2.10 | 2.13 | 4.5 |
| Nicotine polacrilex | 22.22 | 22.22 | 11.11 | 8.33 | 22.22 |
| Sodium carbonate | 4.63 |  | 4.63 | 4.63 |  |
| Potassium bicarbonate | 0.58 |  | 0.58 | 0.58 |  |
| Aspartame |  | 6.00 |  |  |  |
| Acesulfame K | 1.50 |  | 1.50 | 1.50 | 1.50 |
| Flavorant | 31.25 | 1.20 | 31.25 | 31.25 | 31.25 |
| Magnesium stearate | 2.50 | 12.00 | 2.50 | 2.50 | 2.50 |
| Total Weight in mg | 250 | 1200 | 250 | 250 | 482 |

The bioequivalence analysis of a formulation of Example 1 of the present invention versus the traditional comparative lozenge of Example 2 is provided in the following table:

TABLE 2

Bioequivalent Analysis of Example 1 and Example 2

|  | Example 1 | Example 2 | % mean ratio | Confidence Interval (90%) |
|---|---|---|---|---|
| Cmax | 7.23 | 7.58 | 95.4 | 87.4-104.0 |
| AUC (0-t) | 24.40 | 25.64 | 95.2 | 89.5-101.2 |
| AUC (o-inf) | 28.69 | 30.21 | 94.9 | 89.0-101.2 |

Lozenges of the formulations of Examples 1 and 2 were given to 28 subjects. The in vivo dissolution time (the time in which it took patients to consume or dissolve lozenges in their mouths) was recorded after patients reported and examined by clinical personnel to confirm no residues or particles in their oral cavities. The data presented in the following table indicates the faster dissolution that is achieved with the smaller formulations of the present invention.

TABLE 3

Dissolution Time of Lozenges of Example 1 vs. Example 2
In Vivo Dissolution Time (in Minutes)

| Subject No. | Example 1 | Example 2 | Difference |
|---|---|---|---|
| 1 | 8.8 |  |  |
| 2 | 10.4 | 20.8 | 10.4 |
| 3 | 14.1 | 18.6 | 4.5 |
| 4 | 13.9 | 18.9 | 5 |
| 5 | 12.7 | 16 | 3.3 |
| 6 |  | 14 |  |
| 7 | 5.6 | 13.8 | 8.2 |
| 8 | 8.3 |  |  |
| 9 | 11 | 22.8 | 11.8 |
| 10 | 7 | 16.6 | 9.6 |
| 11 | 13.1 | 30.6 | 17.5 |
| 12 | 11.2 | 16.9 | 5.7 |
| 13 | 7.7 | 16.8 | 9.1 |

TABLE 3-continued

Dissolution Time of Lozenges of Example 1 vs. Example 2
In Vivo Dissolution Time (in Minutes)

| Subject No. | Example 1 | Example 2 | Difference |
|---|---|---|---|
| 14 | 8.2 | 16 | 7.8 |
| 15 | 10.8 | 19.8 | 9 |
| 16 | 13.1 | 23.2 | 10.1 |
| 17 | 8.2 | 18.6 | 10.4 |
| 18 | | 7.7 | |
| 19 | 17.4 | 18.4 | 1 |
| 20 | 17.3 | 22 | 4.7 |
| 21 | 25.7 | 38.8 | 13.1 |
| 22 | 12.9 | 22.9 | 10 |
| 23 | 19.3 | 45.6 | 26.3 |
| 24 | 12.1 | 13.8 | 1.7 |
| 25 | 13 | 26.5 | 13.5 |
| 26 | 9.6 | 16.5 | 6.9 |
| 27 | 15.7 | 30.7 | 15 |
| 28 | 20.2 | 26.1 | 5.9 |
| Mean | 12.59 | 21.25 | 9.19 |

What is claimed is:

1. An oral lozenge composition comprising:
   a) a master granule component comprising: at least one an alkaline buffering agent selected from the group consisting of sodium carbonate, sodium bicarbonate, potassium phosphate potassium carbonate and potassium bicarbonate and mixtures thereof; at least one dissolution modifier; and at least one diluent; and
   b) an extragranular component blended with the master granule component comprising a nicotine active and
   at least one alkaline buffering agent selected from the group consisting of sodium carbonate, sodium bicarbonate, potassium phosphate, potassium carbonate and potassium bicarbonate, and mixtures thereof.

2. The oral lozenge composition of claim 1 wherein the master granules are obtained through wet or dry granulation.

3. The oral lozenge composition of claim 1 wherein the at least one dissolution modifier is selected from the group consisting of acacia, agar, alginic acid or a salt thereof, carbomer, carboxymethylcellulose, carrageenan, cellulose, chitosan, copovidone, cyclodextrins, ethylcellulose, gelatin, guar gum, hydroxyethyl cellulose, hydroxyethyl methylcellulose, hydroxypropyl cellulose, hypromellose, inulin, methylcellulose, pectin, polycarbophil or a salt thereof, polyethylene glycol, polyethylene oxide, polyvinyl alcohol, pullulan, starch, tragacanth, trehalose, xanthan gum and mixtures thereof.

4. The oral lozenge composition of claim 3 wherein the at least one dissolution modifier is selected from the group consisting of alginic acid or a salt thereof, polycarbophil or a salt thereof, xanthan gum and mixtures thereof.

5. The oral lozenge composition of claim 4 wherein the at least one dissolution modifier is selected from the group consisting of sodium alginate, calcium polycarbophil, xanthan gum and mixtures thereof.

6. The oral lozenge composition of claim 5 wherein the at least one dissolution modifier is xanthan gum.

7. The oral lozenge of claim 1 wherein the nicotine active is nicotine polacrilex.

8. The oral lozenge of claim 1 wherein the diluent is mannitol.

9. The oral lozenge of claim 1 further comprising at least one optional excipient selected from the group consisting of taste masking agents, sweetening agents, flavorants, chelating agents, antioxidants, glidants or colorants.

10. The oral lozenge of claim 1 wherein the unit weight of the oral lozenge is from about 100 mg to about 500 mg.

11. The oral lozenge of claim 10 wherein the oral lozenge dissolves in less than 15 minutes upon administration to the oral cavity.

12. A nicotine containing lozenge composition with improved user compliance prepared by the process of:
   a) granulating at least one alkaline buffering agent selected from the group consisting of sodium carbonate, sodium bicarbonate, potassium phosphate, potassium carbonate and potassium bicarbonate, and mixtures thereof, at least one dissolution modifier and at least one diluent into a master granulation,
   b) mixing said master granulation with a nicotine active and an alkaline buffering agent selected from the group consisting of sodium carbonate, sodium bicarbonate, potassium phosphate, potassium carbonate and potassium bicarbonate, and mixtures thereof; and
   c) directly compressing said mixture into oral lozenge dosage forms.

13. The nicotine containing lozenge composition with improved user compliance prepared by the process of claim 12 wherein the unit weight of the oral lozenge dosage form is from about 100 mg to about 500 mg.

14. The nicotine containing lozenge composition with improved user compliance prepared by the process of claim 13 wherein the unit weight of the oral lozenge dosage form is about 250 mg.

15. The nicotine containing lozenge composition with improved user compliance prepared by the process of claim 13 wherein the oral lozenge dosage form dissolves in less than 15 minutes upon administration to the oral cavity.

16. The nicotine containing lozenge composition with improved user compliance prepared by the process of claim 12 further comprising at least one optional excipient selected from the group consisting of taste masking agents, sweetening agents, flavorants, chelating agents, antioxidants, glidants or colorants.

17. A nicotine containing lozenge composition which provides increased maximum pH in the oral cavity and fast nicotine absorption prepared by the process of:
   a) granulating at least one alkaline buffering agent selected from the group consisting of sodium carbonate, sodium bicarbonate, potassium phosphate, potassium carbonate and potassium bicarbonate, and mixtures thereof, at least one dissolution modifier and at least one diluent into a master granulation,
   b) mixing said master granulation with a nicotine active and an alkaline buffering agent selected from the group consisting of sodium carbonate, sodium bicarbonate, potassium phosphate, potassium carbonate and potassium bicarbonate, and mixtures thereof; and
   c) directly compressing said mixture into an oral lozenge formulation.

18. The oral lozenge composition of claim 1, wherein the ratio of nicotine active to total buffer is from about 3:1 to about 1:3 by total weight.

19. The oral lozenge composition of claim 1, wherein the ratio of alkaline buffering agent in the extragranular component to alkaline buffering agent in the master granule component is between about 5:1 to about 1:5.

20. The oral lozenge composition of claim 19, wherein the ratio of alkaline buffering agent in the extragranular component to alkaline buffering agent in the master granule component is about 1:1.

21. The oral composition of claim 1, wherein the total amount of alkaline buffering agent is from about 5 mg to about 20 mg.

22. The oral composition of claim 20, wherein the total amount of alkaline buffering agent is from about 8 mg to about 12 mg.

* * * * *